United States Patent [19]
Woo

[11] Patent Number: 6,012,920
[45] Date of Patent: Jan. 11, 2000

[54] ARTICULATING CONNECTOR FOR MANDIBULAR REPOSITIONING ORAL APPLIANCE

[75] Inventor: Stephen Y. Y. Woo, Toronto, Canada

[73] Assignee: Action Win Limited, Toronto, Canada

[21] Appl. No.: 09/296,306

[22] Filed: Apr. 22, 1999

[30] Foreign Application Priority Data

May 5, 1998 [CA] Canada ................................. 2236747

[51] Int. Cl.$^7$ ............................................. A61C 7/00
[52] U.S. Cl. ...................................................... 433/19
[58] Field of Search ................................. 433/18, 19, 6

[56] References Cited

U.S. PATENT DOCUMENTS

| | | | |
|---|---|---|---|
| 4,231,736 | 11/1980 | Reilly | 433/6 |
| 4,472,139 | 9/1984 | Rosenberg | 433/19 |
| 4,505,672 | 3/1985 | Kurz | 433/6 |
| 5,409,017 | 4/1995 | Lowe | 433/36 |
| 5,879,157 | 3/1999 | Scheu | 433/19 |
| 5,919,042 | 7/1999 | Wiliams | 433/19 |

*Primary Examiner*—Todd E. Manahan
*Attorney, Agent, or Firm*—Dimock Stratton Clarizio; Mark B. Eisen

[57] ABSTRACT

An articulating connector for a mandibular repositioning appliance comprises upper and lower housings each pivotally mounted on a pin and rotatable about the axis of the pin, to selectively permit movement of the mandible in the lateral direction. The pins are hingedly connected respectively to threaded adjusting screws to selectively permit movement of the mandible in the vertical direction. The adjusting screws have opposite thread directions and are engaged within a collar, rotation of which sets a desired spacing between the adjusting screws to fix the position of the mandible in the anterior/posterior directions. Optionally the lateral and/or vertical hinges can be locked to restrain lateral and/or vertical movement of the mandible. An appliance embodying the invention can be used to alleviate snoring and sleep apnea, and certain types of temporal mandibular dysfunction, to reposition the mandible in functional appliance therapy such as for CI II patients, for orthodontic treatment of retronagthic mandible, in TMJ pain treatment, and to retain the mandible in a forward opening position wherever limited movement is desired, for example for therapeutic purposes or in post pharyngeal operations and examinations.

20 Claims, 4 Drawing Sheets

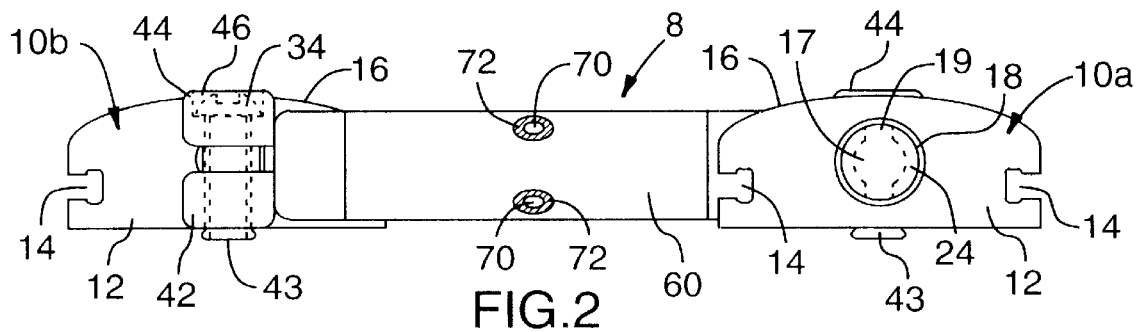
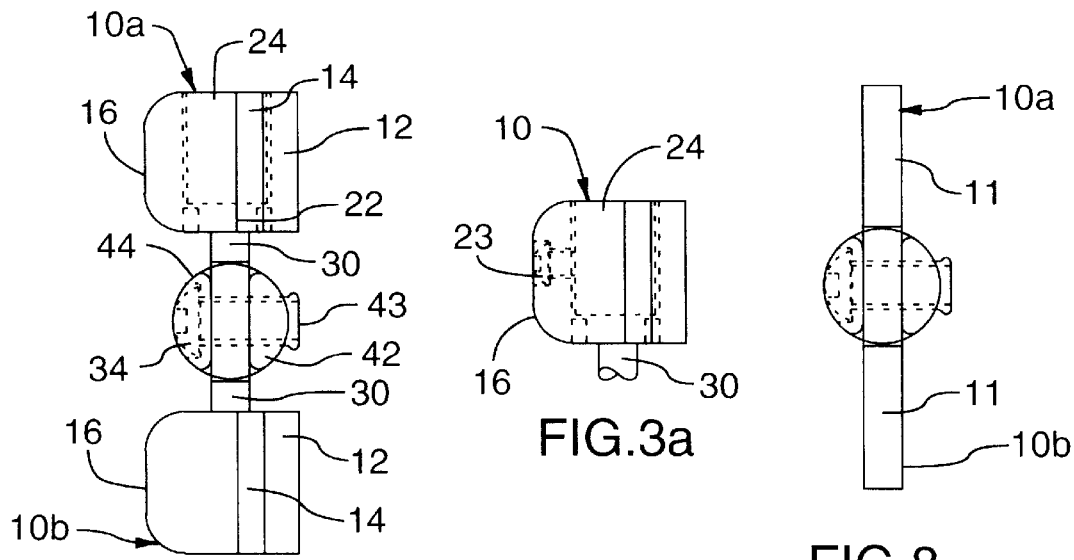
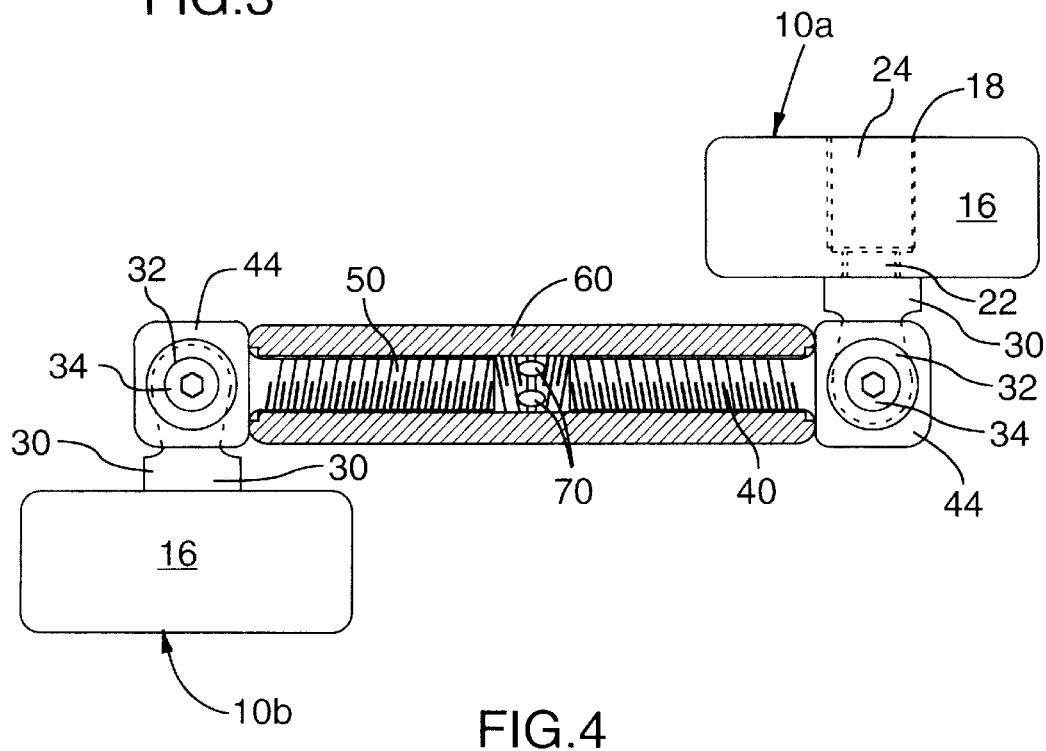

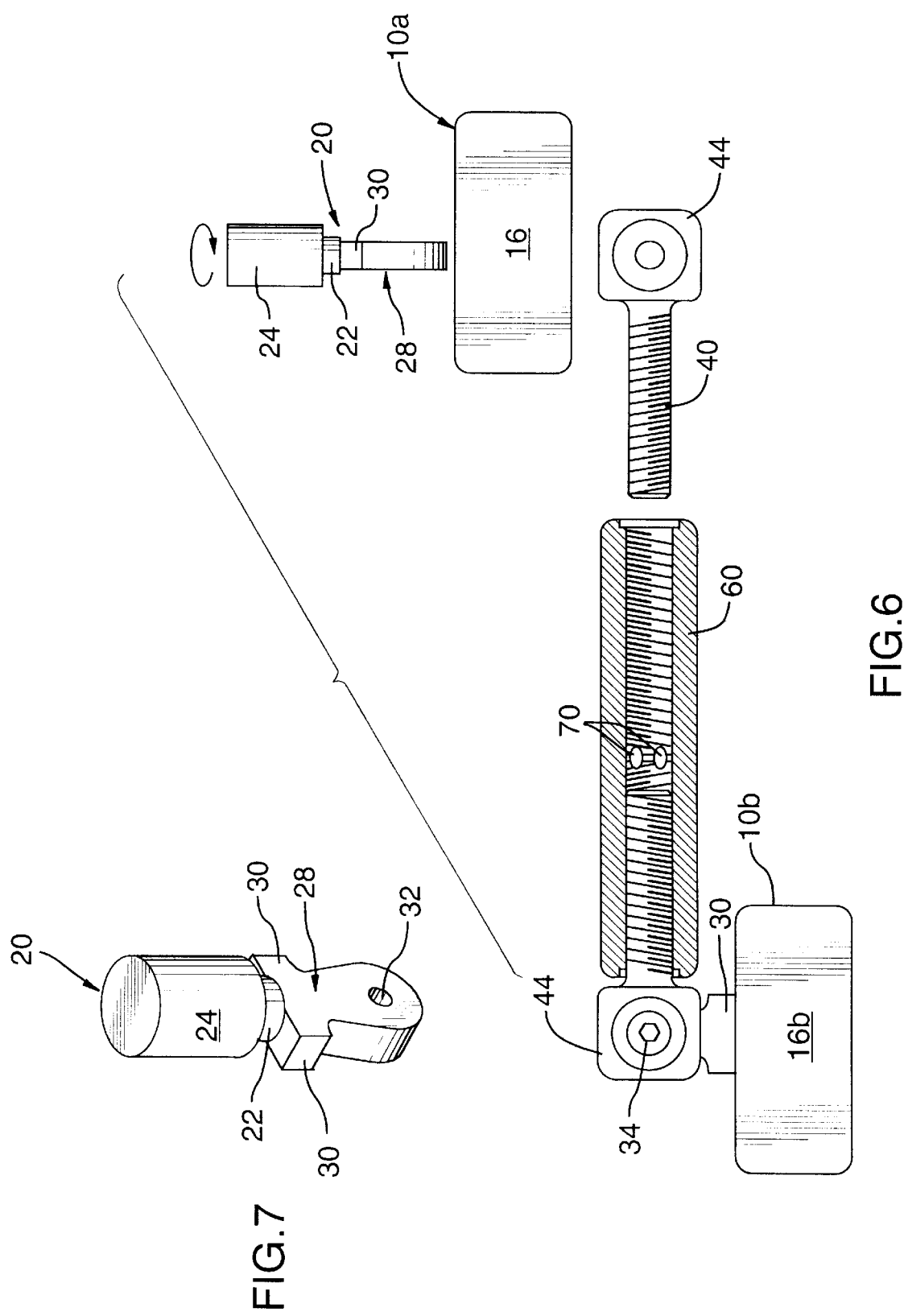

ARTICULATING CONNECTOR FOR MANDIBULAR REPOSITIONING ORAL APPLIANCE

FIELD OF INVENTION

This invention relates to dental appliances. In particular, this invention relates to an articulating connector for a three-way positioning appliance.

BACKGROUND OF THE INVENTION

It is known that improper positioning of the mandible is a common cause of snoring and many sleep disorders related to narrowing of the post pharyngeal space. It is also known to use an oral appliance mounted to a patient's maxillary and mandibular arches, which repositions the mandible to alleviate snoring and sleep disorders.

To alleviate such problems proper positioning of the mandible is critical, and even very minor deviation can severely diminish or defeat the effectiveness of the appliance. Many conventional appliances overextend the mandible, or are otherwise not adjustable in sufficiently fine increments to achieve the optimum setting. Other appliances fix the mandible in a completely rigid position, allowing no movement in the anterior/posterior, lateral or vertical directions, which in many cases can cause mandibular dysfunction. Prior art appliances can also be uncomfortable for the patient, being bulky in the protrusive direction or blocking the tongue from moving anterior of the appliance.

Prior art mandibular repositioners also tend to be difficult to adjust, and require that adjustments be made by a dental professional in order to fix the mandible into the optimum position. This gives rise to an additional expense that must be borne by the patient, which in many cases is unnecessary because the patient is often in the best position to determine the most comfortable and effective setting for the appliance. It would accordingly be advantageous to provide an appliance for alleviating snoring and sleep disorders, which can be easily adjusted by the patient within precise tolerances and which allows lateral or vertical mandibular movement where desirable.

SUMMARY OF THE INVENTION

The invention addresses these and other disadvantages by providing an articulating connector for a mandibular repositioning appliance, which is detachably affixed to trays respectively fitted to the patient's maxillary and mandibular arches and can be easily adjusted in the lateral, vertical and anterior/posterior directions to reposition the mandible within precise tolerances. The appliance is compact and comfortable for the user, and does not interfere with anterior movement of the tongue. After the appliance is fitted the connectors can be adjusted by the patient to maximize comfort and minimize snoring and sleep disorders, avoiding costly visits to a dental professional.

The invention accomplishes this by providing an articulating connector for a mandibular repositioning appliance comprising upper and lower housings each pivotally mounted on a pin and rotatable about the axis of the pin to form a lateral hinge. A lateral hinge lock selectively permits or restrains movement of the mandible in the lateral direction. The pins are each in turn hingedly connected respectively to first and second threaded adjusting screws to form a vertical hinge, which can be fixed by a vertical hinge lock to permit or restrain movement of the mandible in the vertical direction. The adjusting screws have opposite thread directions and are engaged within a collar, rotation of which sets a desired spacing between the adjusting screws, to thus fix a desired position of the mandible in the anterior/posterior directions. The connectors can thereby be adjusted to desired anterior position, with or without freedom of movement in the lateral or vertical directions, to selectively reposition the mandible as required on a case-by-case basis.

The appliance of the invention can be used to alleviate snoring and other sleep disorders; to alleviate certain types of temporal mandibular dysfunction (TMD); to reposition the mandible in functional appliance therapy such as for CI II patients; for orthodontic treatment of retronagthic mandible; in TMJ pain treatment; and to retain the mandible in a forward opening position wherever limited movement is desired, for example for therapeutic purposes or in post pharyngeal operations and examinations.

The present invention thus provides an articulating connector for an oral appliance, comprising an upper housing mounted on an upper pin rotatable in a generally horizontal plane to form a lateral hinge, the upper pin being hingedly connected to a first adjusting screw and rotatable within a generally vertical plane to form a vertical hinge, the first adjusting screw having a helical thread progressing in a first direction, a lower housing mounted on a lower pin rotatable in a generally horizontal plane to form a lateral hinge, the lower pin being hingedly connected to a second adjusting screw and rotatable within a generally vertical plane to form a vertical hinge, the second adjusting screw having a helical thread progressing in a second direction opposite to the first direction, and a collar comprising one end with an axial bore having a helical thread progressing in the first direction for engaging the first screw and another end with an axial bore having a helical thread progressing in the second direction for engaging the second screw, whereby when the upper housing is secured to a maxillary tray and the lower housing is secured to a mandibular tray, upon rotation of the collar a distance between the first and second adjusting screws is selectively increased or decreased to selectively reposition the maxillary tray relative to the mandibular tray in an anterior or posterior direction.

The present invention further provides an oral appliance, comprising a connector having an upper housing mounted on an upper pin rotatable in a generally horizontal plane to form a lateral hinge, the upper pin being hingedly connected to a first adjusting screw and rotatable within a generally vertical plane to form a vertical hinge, the first adjusting screw having a helical thread progressing in a first direction, a lower housing mounted on a lower pin rotatable in a generally horizontal plane to form a lateral hinge, the lower pin being hingedly connected to a second adjusting screw and rotatable within a generally vertical plane to form a vertical hinge, the second adjusting screw having a helical thread progressing in a second direction opposite to the first direction, and a collar comprising one end with an axial bore having a helical thread progressing in the first direction for engaging the first screw and another end with an axial bore having a helical thread progressing in the second direction for engaging the second screw, a maxillary tray having upper housings mounted thereto, and a mandibular tray having lower housings mounted thereto, wherein upon rotation of the collar a distance between the first and second adjusting screws is selectively increased or decreased to selectively reposition the maxillary tray relative to the mandibular tray in an anterior or posterior direction.

BRIEF DESCRIPTION OF THE DRAWINGS

In drawings which illustrate preferred embodiments of the invention by way of example only, FIG. 2 is a top plan view of an articulating connector for the appliance of FIG. 1, FIG. 3 is an end elevation of the connector of FIG. 2, FIG. 3a is an end elevation of an alternate embodiment of the housing for the connector of FIG. 2, FIG. 4 is a side elevation partly in cross-section showing the connector of FIG. 2 in a retracted position, FIG. 6 is a partly exploded elevation of the connector of FIG. 2, FIG. 7 is a perspective view of a preferred embodiment of the pin 20 for the connector of FIG. 2, and FIG. 8 is an end elevation of a further embodiment of the invention omitting the housing.

DETAILED DESCRIPTION OF THE INVENTION

Figure 1:
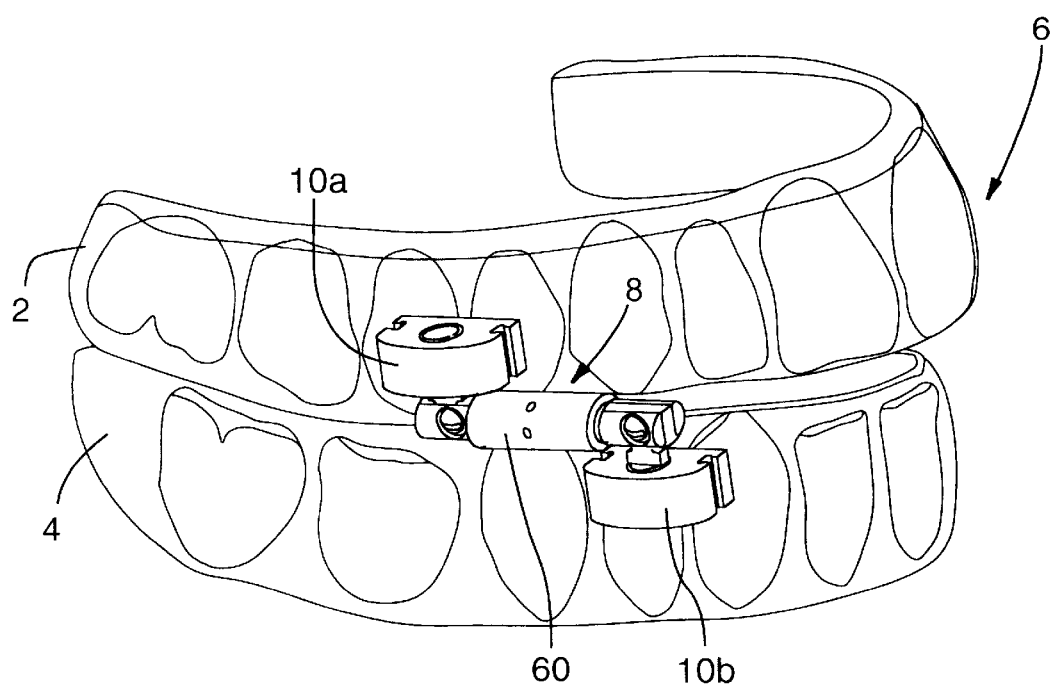
FIG. 1 is a perspective view of the appliance of the invention.

FIG. 1 illustrates a preferred embodiment of an oral appliance 6 according to the invention. The appliance 6 comprises articulating connectors 8 mounted to maxillary and mandibular trays 2, 4 prepared in conventional fashion through a molding process or otherwise. The articulating connectors 8 can be set to fix the mandibular tray 4 in a desired position relative to the maxillary tray 2, to reposition the mandible. The trays 2, 4 may be formed from plastic, for example an acrylic such as Bioacryl (Trademark), or any other suitable material. The components of the articulating connector 8 are preferably composed of medical grade stainless steel or titanium, or a suitable plastic.

The connector 8, illustrated in FIGS. 2 to 6, comprises upper and lower housings 10a, 10b, each provided with a mounting portion 12 which is embedded in the tray 2 or 4 during the molding process and a buccal face 16 which is preferably smooth and convexly curvate for maximum comfort. Preferably a pair of opposed intrusion channels 14, which may be "T"-shaped in cross-section as shown, are disposed in the mounting portions 12 to engage tray material which intrudes into the channels 14 during the molding process and thus ensure that each housing 10 is firmly mounted to the tray 2 or 4.

In the preferred embodiment a hole 18 is bored or formed through the vertical centre of each housing 10 for rotatably mounting the housings 10 on pins 20. The hole 18 has a constricted lower portion 17 with a key slot 19 oriented in the direction of the mounting and buccal faces 12, 16, as shown in phantom in FIG. 2, to allow insertion of the pin 20 as described below.

Each pin 20, illustrated in FIG. 7, preferably comprises a cylindrical stem 22 having a retaining member such as an enlarged head 24 preferably formed integrally with the pin 20. The pin 20 may alternatively be provided with a peg, a "C" washer, snap ring or any other similar structure to retain the housing 10, however a cylindrical enlargement 24 which substantially occupies the entire hole 18 is preferred, for preventing the tray material from seeping into the housing 10 when the connector 8 is embedded into the appliance 6 as described below.

The pin 20 terminates in a flattened portion 28 having opposed projecting shoulders 30 and an eye 32. The flattened portion 28 fits through the slot 19, so that the pin 20 can be assembled to the housing 10 by inserting the eye 32 and shoulders 30 though the slot 19 and rotating the housing 10 approximately 90° so that the shoulders 30 engage beneath the constricted portion 17 of the hole 18. The constricted portion 17 of the hole 18 in the housing 10 is thus trapped between the enlarged head 24 and the shoulders 30, so that the housing 10 is free to rotate about the axis of the pin 20 but is restrained from moving axially along the pin 20. This forms a lateral hinge which allows movement of the upper housing 10a relative to the lower housing 10b in the lateral direction.

When the connector 8 is fully assembled to the trays 2, 4 as described below and the appliance is installed in a patient's mouth, the housing 10 cannot rotate far enough on the pin 20 that the shoulders 30 come into alignment with the slot 19, so the housing 10 cannot inadvertently disengage from the pin 20. The preferred embodiment thus allows for easy assembly of the connector 8, however it will be appreciated that there are many other ways to rotationally engage the housing 10 to the pin 20. For example, the housings 10 may be mounted on a sphere (not shown) in a ball-socket joint fashion, the object being to allow the housing 10 to rotate freely in a lateral plane.

Optionally a lateral hinge lock can be provided, as shown in FIG. 3a, comprising a fastening member such as locking bolt 23 disposed through a threaded hole 17 extending through the buccal face 16 of the housing 10 and into the hole 18. Tightening the locking bolt 23 thus engages the locking bolt 23 against the head 24 of the pin 20, to restrain the housing 10 against rotation about the axis of the pin 20, i.e. the housing 10 becomes rotationally locked to the stem 22 of the pin 20. When the locking bolts 23 of both the upper and lower housings 10a, 10b are tightened, lateral movement of the mandibular tray 4 relative to the maxillary tray 2 is prevented. However, in most cases the patient will be more comfortable if lateral movement of the mandible is available, by allowing the housings 10 to rotate freely on the pins 20.

Figure 5:
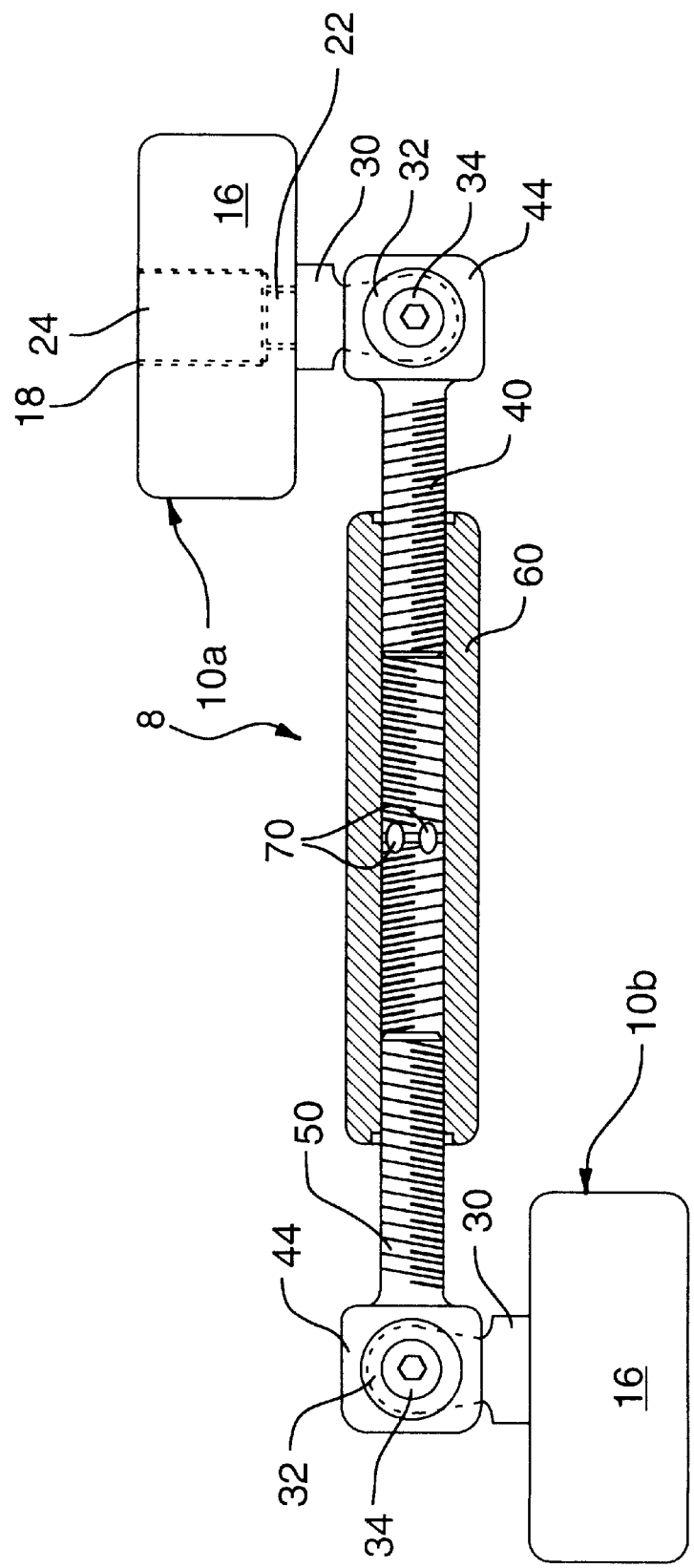
FIG. 5 is a side elevation partly in cross-section showing the connector of FIG. 2 in an extended position.

The pins 20 are each hingedly connected to an anterior adjusting screw 40 or 50 to form a vertical hinge. The pins 20 are thus rotatable within a vertical plane in the direction of the axis of the screw 40 or 50. One end of a first anterior adjusting screw 40 is provided with opposed arms 42, 44 for receiving the eye 32 of the upper pin 20a, one arm 42 having a threaded insert or nut 43 and the other arm 44 having an opening 45. The first anterior adjusting screw 40 is provided with a helical thread progressing in a first direction, for example clockwise, as shown in FIGS. 4 and 5.

A bolt 34 is engaged through the opening 45, through the eye 32 and into the threaded insert 43 to pivotally attach the upper pin 20a to the adjusting screw 40. Preferably the arm 44 has a countersuik or recessed portion 46 into which the head 35 of the locking bolt 34 is received, to avoid protrusion into the buccal region. Optionally the bolt 34 can be tightened to clamp the arms 42, 44 together and fix the pin 20 at a selected attitude relative to the adjusting screw 40, and thus form a vertical hinge lock restraining vertical movement of the mandible. This feature is useful, for example, to retain the mandible in a forward opening position for post pharyngeal operations and examinations. However, in most cases the vertical hinge lock is unnecessary as allowing vertical movement of the mandible will achieve the desired result and will be more comfortable for the patient.

The lower pin 20b is likewise hingedly connected to opposed arms 42, 44 provided at one end of a second anterior adjusting screw 50, for receiving the eye 32 of the lower pin 20b. The second anterior adjusting screw 50 is provided with a helical thread progressing in a second direction opposite to that of the first anterior adjusting screw 40, for example counterclockwise, as shown in FIGS. 4 and 5.

The first and second anterior adjusting screws 40, 50 are engaged within a collar 60. One end of the collar 60 is provided with an axial bore 62 having an internal clockwise helical thread progressing in the first direction (clockwise in the example given) for engaging the thread of the first adjusting screw 40. The opposite end of the collar 60 has an axial bore 64 having a helical thread progressing in the second direction (counterclockwise in the example given) for engaging the thread of the second adjusting screw 50. Thus, rotation of the collar 60 in one direction retracts both screws 40, 50 into the collar 60 simultaneously to decrease the distance between the screws 40, 50, and rotation in the other direction extends both screws 40, 50 from the collar 60 simultaneously to increase the distance between the screws 40, 50. FIG. 4 illustrates the connector 8 with the adjusting screws 40, 50 in a fully retracted position, and FIG. 5 illustrates the connector 8 with the adjusting screws 40, 50 in an extended position. The collar 60 preferably has a knurled or other high-friction surface along at least a portion of its exterior wall 66, to facilitate gripping and rotating the collar 60 when the appliance 6 is in the patient's mouth.

In operation, a dental professional takes impressions of the patient's maxillary and mandibular arches using conventional techniques. From the impressions a dental laboratory molds the maxillary and mandibular trays 2, 4, embedding the housings 10a into the buccal face of the maxillary tray 2 and embedding the housings 10b into the buccal face of the mandibular tray 4, preferably so that the plastic or other tray material intrudes into the channels 14 and about the entire housing 10 to securely affix the housings 10 to the tray 2 or 4. For most apnea and other sleep disorder applications the upper housings 10a are preferably located adjacent to the 2nd premolars with the vertical locking hinges situated below the cusps, and the lower housings 10b are preferably located adjacent to the canines with the vertical locking hinges situated above the cusps. The housings 10 may be otherwise located according to the particular requirements of the patient.

Pins 20 are attached to the housings 10, and the adjusting screws 40, 50 are assembled to the eyes 32 of pins 20 and the threaded ends of the screws 40, 50 are aligned with the complimentary threaded bores 62, 64 in the collar 60. The collar 60 is rotated in the appropriate direction to retract the screws 40, 50 into their respective threaded bores 62, 64. The trays 2, 4 are thus secured together to form the appliance 6, the relative positions and orientations of the trays 2, 4 being determined by the rotational orientation of the housings 10 on the pins 20, the attitudes of the pins 20 relative to the adjusting screws 40, 50, and the distance between the adjusting screws 40, 50 as set by the rotatable collar 60.

The anterior adjusting screws 40, 50 prevent movement of the mandible in the anterior/posterior directions. The mandibular tray 4 is fixed in a selected forward position relative to the maxillary tray 2 by rotating the collar 60 to either increase or decrease the distance between the screws 40, 50. Preferably the screws 40, 50 and collar 60 are long enough to permit at least 8 mm of movement of the mandibular tray 4 relative to the maxillary tray 2 in the anterior/posterior directions. The inner ends of the adjusting screws 40, 50 may be crimped or clinched to prevent the screws 40, 50 from being extracted from the collar 60.

At the same time, mandibular movement can be available in the lateral and vertical directions. The lateral hinges (i.e. rotation of the housings 10 on the pins 20) allow lateral movement of the mandibular tray 4 relative to the maxillary tray 2, and the vertical hinges (i.e. the connections between the pins 20 and the adjusting screws 40, 50) allow vertical movement because the trays 2, 4 are free to pivot at the vertical hinge connection with the anterior adjusting screws 40, 50. As noted above, movement in the lateral and/or vertical directions can be selectively restrained if desired using the lateral and/or vertical hinge locks so described.

The dentist or other dental professional fits the appliance 6 to the patient, and adjusts the appliance 6 to the desired position for the particular disorder sought to be relieved. The dentist determines which directions of motion should be available to the patient, and locks the lateral and/or vertical hinges if desirable to restrain movement in one or both of these directions. The patient can be instructed to adjust the appliance in the anterior/posterior directions to maximize comfort and relief from the disorder, by rotating the rotatable collar 60 to increase or decrease the distance between the screws 40, 50. To facilitate this, the collar 60 may be provided with holes 70 as shown in FIG. 2, preferably at 90° intervals around the collar 60, for the insertion of a small tool (not shown) that assists in rotating the collar 60. Optionally coloured calibration markings 72 can be provided to assist the user in determining the extent of movement of the adjusting screws 40, 50. For example, the pitch of the thread inside the collar 60 could be selected so that one full turn of the collar 60 extends or retracts the adjusting screws 40, 50 by exactly one millimetre. Thus, by observing the colour of the calibration markings 72 when rotating the collar 60 the user will know how much the collar 60 has been rotated, and will thus know how far the adjusting screws 40, 50 have been adjusted.

To retain the mandible in a forward opening position for post pharyngeal operations and examinations, the pins 20 are aligned at a wide obtuse angle relative to the screws 40, 50 and the clamping bolts 34 are tightened to fix the vertical hinges and prop the mandible in the forward opening position. Fine adjustments can be made by the dentist by rotating the collar 60 to further increase or decrease the distance between the screws 40, 50 and thus, in this case, the vertical spacing between the maxillary and mandibular trays 2, 4. For such applications it may not be necessary to use trays 2, 4 which are specifically fitted to the patient's maxillary and mandibular arches, because the appliance 6 is used for a relatively short interval and the pressure exerted by the arches against the trays 2, 4 when the mouth is in such an open position will prevent the appliance 6 from becoming dislodged.

FIG. 8 illustrates a further embodiment of the invention in which the upper and lower housings 10a, 10b each comprise a plate 11 which is completely embedded into the side surfaces of the tray 2 or 4, respectively. This eliminates the possibility of irritation due to projections from the buccal face of the tray 2 or 4. The operation of this embodiment is otherwise the same as the previously described embodiment.

Preferred embodiments of the invention having been thus described by way of example, it will be apparent to those skilled in the art that modifications and adaptations may be made without departing from the scope of the invention, as set out in the appended claims.

I claim:

1. An articulating connector for an oral appliance, comprising an upper housing mounted on an upper pin rotatable in a generally horizontal plane to form a lateral hinge, the upper pin being hingedly connected to a first adjusting screw and rotatable within a generally vertical plane to form a vertical hinge, the first adjusting screw having a helical thread progressing in a first direction, a lower housing mounted on a lower pin rotatable in a generally horizontal plane to form a lateral hinge, the lower pin being hingedly connected to a second adjusting screw and rotatable within a generally vertical plane to form a vertical hinge, the second adjusting screw having a helical thread progressing in a second direction opposite to the first direction, and a collar comprising one end with an axial bore having a helical thread progressing in the first direction for engaging the first screw and another end with an axial bore having a helical thread progressing in the second direction for engaging the second screw, whereby when the upper housing is secured to a maxillary tray and the lower housing is secured to a mandibular tray, upon rotation of the collar a distance between the first and second adjusting screws is selectively increased or decreased to selectively reposition the maxillary tray relative to the mandibular tray in an anterior or posterior direction.

2. The connector of claim 1 including vertical hinge locks for selectively restraining rotation of the upper pin and the lower pin relative to the first and second adjusting screws, respectively.

3. The connector of claim 2 in which each lateral hinge lock comprises a bolt threadedly engaged through one end of the upper pin and one end of the adjusting screw, which when tightened engages rotationally fixes the upper pin to the adjusting screw.

4. The connector of claim 1 in which at least a portion of an outer wall of the collar is provided with a high-friction surface to facilitate gripping the collar for rotation.

5. The connector of claim 1 in which a wall of the collar is provided with markings to indicate a position of the first adjusting screw or the second adjusting screw or both within the collar.

6. The connector of claim 1 affixed to a maxillary or mandibular tray.

7. The connector of claim 6 in which the maxillary or mandibular tray is formed from an impression of a maxillary or mandibular arch, respectively.

8. The connector of claim 7 in which the housings are provided with intrusion channels for engaging material of a maxillary or mandibular tray during a molding process.

9. The connector of claim 1 including lateral hinge locks for selectively restraining rotation of the upper housing and the lower housing relative to the upper pin and the lower pin, respectively.

10. The connector of claim 9 in which each lateral hinge lock comprises a bolt threadedly engaged into the housing and extending to the upper pin, which when tightened engages against the upper pin to prevent rotation of the housing.

11. An oral appliance, comprising a connector having an upper housing mounted on an upper pin rotatable in a generally horizontal plane to form a lateral hinge, the upper pin being hingedly connected to a first adjusting screw and rotatable within a generally vertical plane to form a vertical hinge, the first adjusting screw having a helical thread progressing in a first direction, a lower housing mounted on a lower pin rotatable in a generally horizontal plane to form a lateral hinge, the lower pin being hingedly connected to a second adjusting screw and rotatable within a generally vertical plane to form a vertical hinge, the second adjusting screw having a helical thread progressing in a second direction opposite to the first direction, and a collar comprising one end with an axial bore having a helical thread progressing in the first direction for engaging the first screw and another end with an axial bore having a helical thread progressing in the second direction for engaging the second screw, a maxillary tray having upper housings mounted thereto, and a mandibular tray having lower housings mounted thereto, wherein upon rotation of the collar a distance between the first and second adjusting screws is selectively increased or decreased to selectively reposition the maxillary tray relative to the mandibular tray in an anterior or posterior direction.

12. The appliance of claim 11 including vertical hinge locks for selectively restraining rotation of the upper pin and the lower pin relative to the first and second adjusting screws, respectively.

13. The appliance of claim 12 in which each lateral hinge lock comprises a bolt threadedly engaged through one end of the upper pin and one end of the adjusting screw, which when tightened engages rotationally fixes the upper pin to the adjusting screw.

14. The appliance of claim 11 in which at least a portion of an outer wall of the collar is provided with a high-friction surface to facilitate gripping the collar for rotation.

15. The appliance of claim 11 in which a wall of the collar is provided with markings to indicate a position of the first adjusting screw or the second adjusting screw or both within the collar.

16. The appliance of claim 11 in which the maxillary or mandibular tray is formed from an impression of a maxillary or mandibular arch, respectively.

17. The appliance of claim 16 in which the housings are provided with intrusion channels for engaging material of a maxillary or mandibular tray during a molding process.

18. The appliance of claim 11 in which the mandibular tray can be positioned relative to the maxillary tray within a range of at least 8 mm.

19. The appliance of claim 11 including lateral hinge locks for selectively restraining rotation of the upper housing and the lower housing relative to the upper pin and the lower pin, respectively.

20. The appliance of claim 19 in which each lateral hinge lock comprises a bolt threadedly engaged into the housing and extending to the upper pin, which when tightened engages against the upper pin to prevent rotation of the housing.

* * * * *